(12) United States Patent
Hahn

(10) Patent No.: US 11,179,569 B2
(45) Date of Patent: Nov. 23, 2021

(54) PACING METHOD AND SYSTEM FOR CARDIOPROTECTION DURING CHEMOTHERAPY

(71) Applicant: Cardiac Pacemakers, Inc., St. Paul, MN (US)

(72) Inventor: Stephen J. Hahn, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 92 days.

(21) Appl. No.: 16/576,141

(22) Filed: Sep. 19, 2019

(65) Prior Publication Data

US 2020/0094053 A1 Mar. 26, 2020

Related U.S. Application Data

(60) Provisional application No. 62/734,539, filed on Sep. 21, 2018.

(51) Int. Cl.
| | | |
|---|---|---|
| *A61N 1/362* | (2006.01) | |
| *A61N 1/365* | (2006.01) | |
| *A61N 1/372* | (2006.01) | |
| *A61N 1/375* | (2006.01) | |

(52) U.S. Cl.
CPC ....... *A61N 1/3629* (2017.08); *A61N 1/36535* (2013.01); *A61N 1/36542* (2013.01); *A61N 1/36585* (2013.01); *A61N 1/36592* (2013.01); *A61N 1/3756* (2013.01); *A61N 1/37211* (2013.01); *A61N 1/37512* (2017.08)

(58) Field of Classification Search
None
See application file for complete search history.

(56) References Cited

U.S. PATENT DOCUMENTS

| | | | |
|---|---|---|---|
| 5,360,437 A | * | 11/1994 | Thompson ......... A61N 1/37211 607/30 |
| 7,295,874 B2 | | 11/2007 | Prinzen et al. |
| 7,366,568 B2 | | 4/2008 | Pastore et al. |
| 7,437,191 B2 | | 10/2008 | Pastore et al. |
| 7,532,933 B2 | | 5/2009 | Hastings et al. |
| 7,647,109 B2 | | 1/2010 | Hastings et al. |
| 7,650,186 B2 | | 1/2010 | Hastings et al. |
| 7,668,594 B2 | | 2/2010 | Marina et al. |
| 7,711,420 B2 | | 5/2010 | Baynham et al. |
| 7,774,057 B2 | | 8/2010 | Pastore et al. |
| 7,885,710 B2 | | 2/2011 | Sih et al. |
| 7,894,896 B2 | | 2/2011 | Tamara et al. |
| 7,917,210 B2 | | 3/2011 | Baynham et al. |
| 7,962,208 B2 | | 6/2011 | Shuros et al. |

(Continued)

*Primary Examiner* — Brian T Gedeon
(74) *Attorney, Agent, or Firm* — Schwegman Lundberg & Woessner, P.A.

(57) ABSTRACT

An example of a system and method for protecting a patient diagnosed of cancer from cardiac injury resulting from a chemotherapy treating the cancer. A sequence of cardioprotective pacing sessions may be initiated based on timing of the chemotherapy. Cardiac pacing pulses may be delivered to the patient during each session of the cardioprotective pacing sessions according to a cardioprotective pacing mode for controlling delivery of the cardiac pacing pulses to effect cardioprotection against potential myocardial injury resulting from the chemotherapy. The cardioprotective pacing mode may specifying alternating non-pacing and pacing periods.

20 Claims, 9 Drawing Sheets

(56) References Cited

U.S. PATENT DOCUMENTS

| | | |
|---|---|---|
| 8,140,155 B2 | 3/2012 | Zielinski et al. |
| 8,412,326 B2 | 4/2013 | Arcot-Krishnamurthy et al. |
| 8,452,400 B2 * | 5/2013 | Shuros ............... A61B 18/1492 |
| | | 607/9 |
| 8,483,826 B2 | 7/2013 | Zielinski et al. |
| 8,548,586 B2 | 10/2013 | Arcot-Krishnamurthy et al. |
| 8,615,296 B2 | 12/2013 | Pastore et al. |
| 8,644,934 B2 | 2/2014 | Hastings |
| 8,805,497 B2 | 8/2014 | Dong et al. |
| 8,812,104 B2 | 8/2014 | Mokelke et al. |
| 8,958,873 B2 | 2/2015 | Arcot-Krishnamurthy et al. |
| 2008/0071315 A1 * | 3/2008 | Baynham ........... A61N 1/36514 |
| | | 607/3 |
| 2008/0221636 A1 * | 9/2008 | Pastore ............... A61N 1/36514 |
| | | 607/18 |
| 2014/0379041 A1 | 12/2014 | Foster |
| 2015/0057558 A1 | 2/2015 | Stahmann et al. |
| 2015/0088155 A1 | 3/2015 | Stahmann et al. |

* cited by examiner

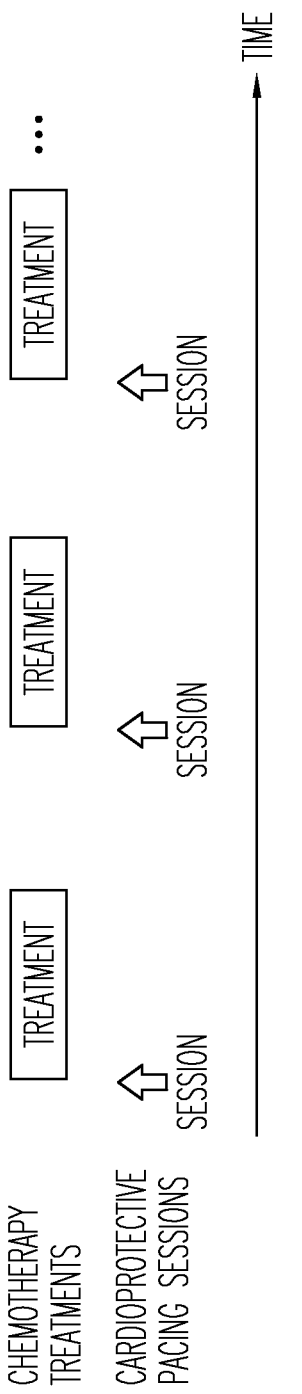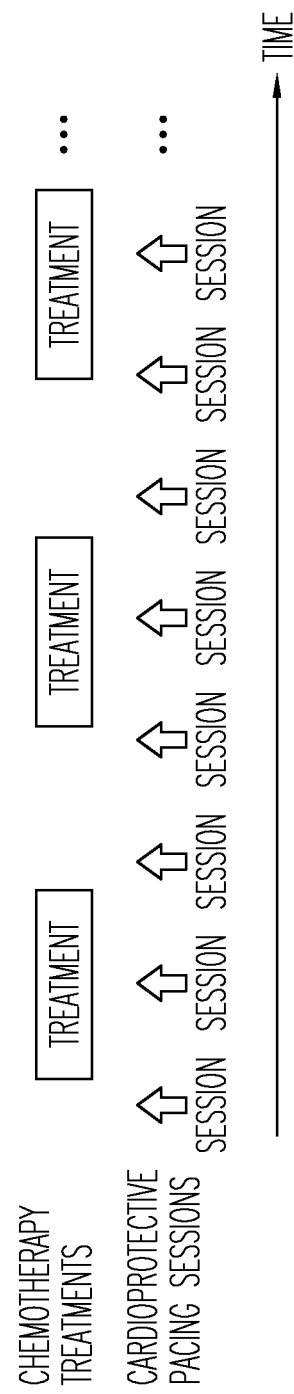

PACING METHOD AND SYSTEM FOR CARDIOPROTECTION DURING CHEMOTHERAPY

CLAIM OF PRIORITY

This application claims the benefit of priority under 35 U.S.C. § 119(e) of U.S. Provisional Patent Application Ser. No. 62/734,539, filed on Sep. 21, 2018, which is herein incorporated by reference in its entirety.

TECHNICAL FIELD

This document relates generally to cardiac pacing and more particularly to a method and system for providing cardioprotective pacing to cancer patients receiving chemotherapy.

BACKGROUND

Chemotherapy is a type of widely used cancer therapy known for its efficacy as well as side effects. Cardiovascular dysfunctions are among the significant side effects of chemotherapy drugs. For example, anthracyclines are a class of chemotherapy agents (e.g., doxorubicin, daunorubicin, idarubicin, and epirubicin) commonly applied to treat various types of cancers while being particularly known for cardiotoxicity. Measurable cardiac dysfunctions have been reported in many cancer patients receiving anthracycline-based chemotherapies. Cardiac damage due to the cardiotoxicity is believed to create an underlying substrate for later progression of left ventricular dysfunction (e.g., measured by low ejection fraction) and heart failure. Mortality during and after chemotherapies can be significantly increased by cardiovascular diseases including congestive heart failure.

It is recently estimated that more than 125,000 cancer patients are treated with anthracyclines in the U.S. Cardiotoxicity is cited as a major limitation to dosage, efficacy, and usage of anthracyclines. Anthracycline-based chemotherapies may be more efficaciously utilized for cancer treatment if the associated cardiotoxic side effects can be reduced.

SUMMARY

An example (e.g., "Example 1") of a system for delivering cardiac pacing pulses to a patient diagnosed of cancer and receiving chemotherapy treating the cancer may include an implantable cardioprotective pacemaker pre-configured for operation only under a cardioprotective pacing mode for controlling delivery of the cardiac pacing pulses to effect cardioprotection against potential myocardial injury resulting from chemotherapy. The cardioprotective pacing mode may specify alternating non-pacing and pacing periods. The non-pacing periods each include a non-pacing duration during which none of the cardiac pacing pulses is timed to be delivered. The pacing periods each include a pacing duration during which a plurality of pacing pulses of the cardiac pacing pulses is timed to be delivered. The pacemaker may not be reconfigurable for delivering the cardiac pacing pulses according to a pacing mode other than the cardioprotective pacing mode.

In Example 2, the subject matter of Example 1 may optionally be configured such that the pacemaker has a programmability limited to adjusting parameters used for controlling delivery of the cardiac pacing pulses under the cardioprotective pacing mode.

In Example 3, the subject matter of any one or any combination of Examples 1 and 2 may optionally be configured such that the pacemaker is an implantable leadless pacemaker configured for intracardiac placement a percutaneous transluminal procedure.

In Example 4, the subject matter of any one or any combination of Examples 1 to 3 may optionally be configured such that the pacemaker include a pacing output circuit configured to deliver the cardiac pacing pulses and a control circuit configured to control the delivery of the cardiac pacing pulses using the pacing parameters according to the cardioprotective pacing mode. The control circuit includes a sequence initiator configured to initiate the sequence of cardioprotective pacing sessions in response to the sequence starting command and a command receiver configured to receive the sequence starting command.

In Example 5, the subject matter of Example 4 may optionally be configured to further include an external device configured to wirelessly communicate with the pacemaker and to generate the sequence starting command.

In Example 6, the subject matter of Example 5 may optionally be configured such that the external device includes a magnet.

In Example 7, the subject matter of Example 5 may optionally be configured such that the external device includes a programmable electronic device.

In Example 8, the subject matter of any one or any combination of Examples 4 to 7 may optionally be configured such that the control circuit further includes a sequence timer configured to initiate each session of the sequence of cardioprotective pacing sessions after the initiation of the sequence of cardioprotective pacing sessions and a session timer configured to time the pacing and non-pacing periods during the each session in response to the initiation of the each session.

In Example 9, the subject matter of Example 8 may optionally be configured such that the sequence timer is configured to initiate the each session in response to a session starting command, and the command receiver is further configured to receive the session starting command.

In Example 10, the subject matter of any one or any combination of Examples 8 and 9 may optionally be configured such that the control circuit further includes a memory circuit configured to store information required to operate the pacemaker under the cardioprotective pacing mode, the information includes the pacing parameters and a pacing sessions schedule, and the sequence timer is configured to initiate the each session according to the stored pacing sessions schedule.

In Example 11, the subject matter of any one or any combination of Examples 4 to 10 may optionally be configured such that the pacemaker further includes a sensing circuit configured to sense one or more cardiac signals from the patient, and the control circuit further includes a parameter adjuster to adjust the pacing parameters based on the sensed one or more cardiac signals such that the delivery of the cardiac pacing pulses effects the cardioprotection against potential myocardial injury resulting from the chemotherapy.

In Example 12, the subject matter of Example 11 may optionally be configured to further include one or more sensors configured to sense one or more patient state signals, and such that the control circuit further includes an event detector configured to detect an inhibit event using the one or more signals, and the parameter adjuster is configured to inhibit or reschedule the delivery of the cardiac pacing pulses during a session of the sequence of cardioprotective pacing session in response to a detection of the inhibiting event.

In Example 13, the subject matter of Example 12 may optionally be configured such that the one or more sensors include a heart rate sensor configured to sense the patient's heart rate and the event detector is configured to detect the inhibit event when the sensed heart rate exceeds an upper threshold or falls below a lower threshold.

In Example 14, the subject matter of any one or any combination of Examples 12 and 13 may optionally be configured such that the one or more sensors include a posture sensor configured to sense the patient's posture and the event detector is configured to detect the inhibit event when the sensed posture indicates that the patient is at an upright posture.

In Example 15, the subject matter of any one or any combination of Examples 12 to 14 may optionally be configured such that the one or more sensors include an activity sensor configured to sense the patient's physical activity level, and the event detector is configured to detect the inhibit event when the sensed activity level exceeds a threshold activity level.

An Example (e.g., "Example 16") of a method for protecting a patient diagnosed of cancer from cardiac injury resulting from a chemotherapy treating the cancer is also provided. The method may include initiating a sequence of cardioprotective pacing sessions based on timing of the chemotherapy and delivering cardiac pacing pulses to the patient during each session of the cardioprotective pacing sessions according to a cardioprotective pacing mode for controlling delivery of the cardiac pacing pulses to effect cardioprotection against potential myocardial injury resulting from the chemotherapy. The cardioprotective pacing mode may specify alternating non-pacing and pacing periods. The non-pacing periods each include a non-pacing duration during which none of the cardiac pacing pulses is timed to be delivered. The pacing periods each include a pacing duration during which a plurality of pacing pulses of the cardiac pacing pulses is timed to be delivered.

In Example 17, the subject matter of delivering the cardiac pacing pulses as found in Example 16 may optionally include delivering the cardiac pacing pulses from an implantable pacemaker, and the subject matter of initiating the sequence of cardioprotective pacing sessions as found in Example 16 may optionally include initiating the sequence of cardioprotective pacing sessions is response to a sequence starting command received by the implantable pacemaker.

In Example 18, the subject matter of delivering the cardiac pacing pulses from the implantable pacemaker as found in Example 17 may optionally include delivering the cardiac pacing pulses from an implanted intracardiac leadless pacemaker.

In Example 19, the subject matter of any one or any combination of Examples 16 to 18 may optionally include determining the timing of the chemotherapy including a chemotherapy starting time, and the subject matter of initiating the sequence of cardioprotective pacing sessions as found in any one or any combination of Examples 16 to 18 may optionally include initiating the sequence of cardioprotective pacing sessions at a beginning of a pre-chemotherapy duration ending with the chemotherapy starting time In Example 20, the subject matter of determining the timing of the chemotherapy as found in Example 19 may optionally further include determining a chemotherapy ending time, and the subject matter of Example 19 may optionally further include ending the sequence of cardioprotective pacing sessions at an end of a post-chemotherapy duration starting with the chemotherapy ending time.

In Example 21, the subject matter of any one or any combination of Examples 16 to 20 may optionally further include initiating each session of the sequence of cardioprotective pacing sessions according to a session frequency.

In Example 22, the subject matter of the chemotherapy as found in any one or any combination of Examples 19 to 21 may optionally include a series treatments, the subject matter of determining the timing of the chemotherapy as found in any one or any combination of Examples 19 to 21 may optionally include determining a time for applying each treatment of the series of treatments, and the subject matter of any one or any combination of Examples 19 to 21 may optionally further include further include initiating one or more sessions of the sequence of cardioprotective pacing sessions based on the time for applying the each treatment.

In Example 23, the subject matter of initiating the one or more sessions as found in Example 22 may optionally include initiating one session of the one or more sessions before the each treatment starts.

In Example 24, the subject matter of initiating the one or more sessions as found in any one or any combination of Examples 22 and 23 may optionally include initiating one session of the one or more sessions after the each treatment ends.

In Example 25, the subject matter of any one or any combination of Examples 16 to 24 may optionally further include sensing one or more cardiac signals and adjusting one or more pacing parameters for effecting the cardioprotection against potential myocardial injury resulting from the chemotherapy based on the sensed one or more cardiac signals. The one or more pacing parameters control the delivery of the cardiac pacing pulses according to the cardioprotective pacing mode.

In Example 26, the subject matter of Example 25 may optionally further include detecting a heart rate from the one or more cardiac signals, and the subject matter of adjusting the one or more pacing parameters as found in Example 25 may optionally include setting a pacing rate to a rate substantially higher than the detected heart rate.

In Example 27, the subject matter of any one or any combination of Examples 25 and 26 may optionally further include detecting an intrinsic atrioventricular interval from the one or more cardiac signals, and the subject matter of adjusting the one or more pacing parameters as found in any one or any combination of Examples 25 and 26 may optionally include setting an atrioventricular delay to a time interval substantially shorter than the detected intrinsic atrioventricular interval.

In Example 28, the subject matter of any one or any combination of Examples 16 to 27 may optionally further include sensing one or more signals from the patient, detecting an inhibiting event using the sensed one or more signals, and inhibiting or rescheduling the delivery of the cardiac pacing pulses during the sequence of cardioprotective pacing session in response to a detection of the inhibiting event.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense.

The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 7 is a timing diagram illustrating an embodiment of cardioprotective pacing sessions each timed based on a treatment of a chemotherapy.

FIG. 8 is a timing diagram illustrating an embodiment of cardioprotective pacing sessions timed to be applied periodically.

DETAILED DESCRIPTION

Figure 1:
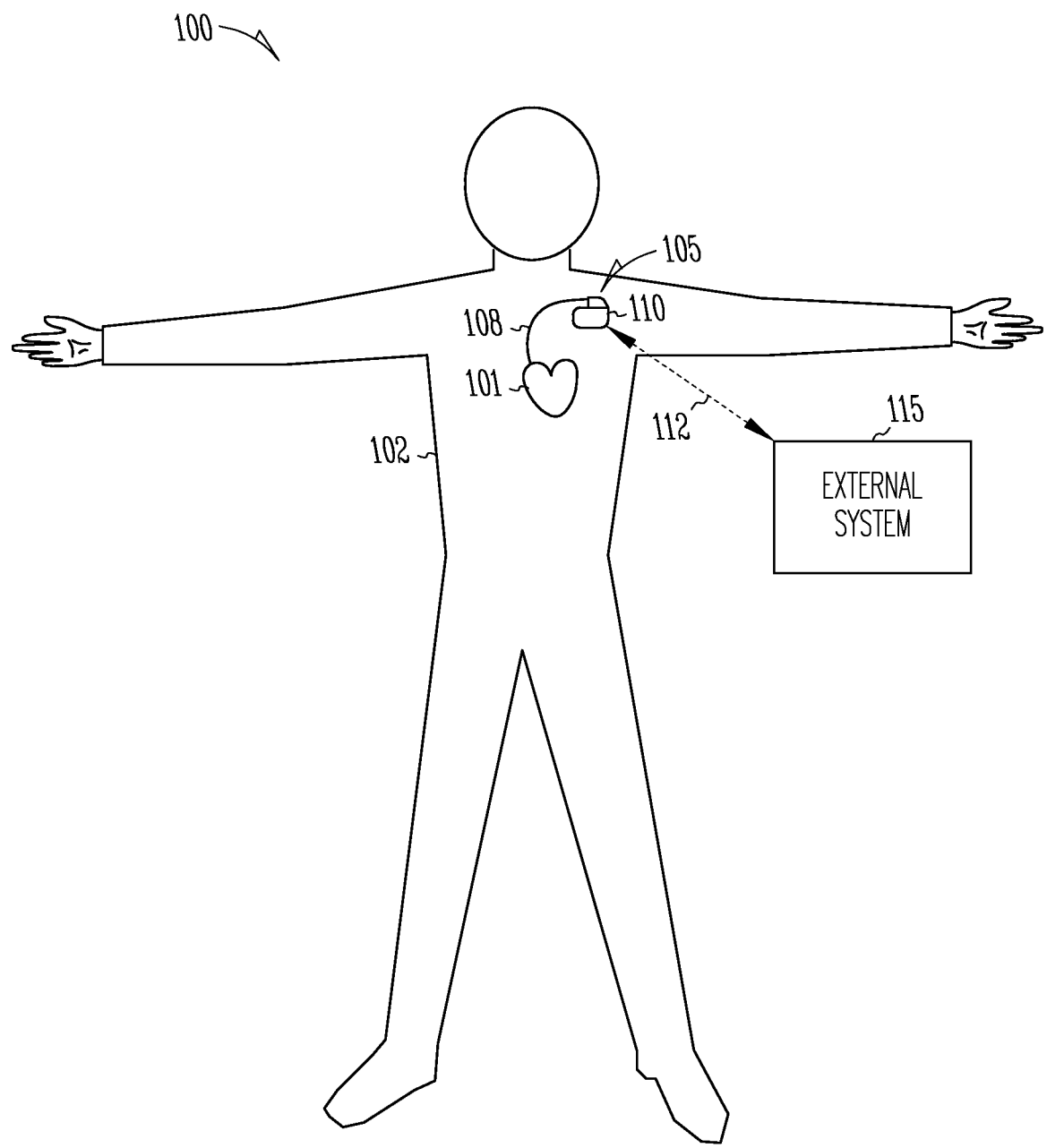
FIG. 1 is an illustration of an embodiment of a cardioprotective pacing system and portions of an environment in which the system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a method and system for delivering cardiac pacing to a cancer patient being treated by chemotherapy to protect the patient from drug-induced cardiac damage and potentially heart failure. Many chemotherapy agents, with anthracyclines being a particular example, are known for cardiotoxicity causing cardiac damages leading to cardiovascular dysfunctions and eventually heart failure.

Various methods have been developed for preventing or reducing cardiac damages caused by cardiac ischemia. Such methods use various types of stimulation to induce cardioprotective signaling in a patient, thereby activating or augmenting the patient's natural cardioprotective mechanism. For example, brief periods of ischemia are known to elicit cellular signaling changes that can protect a patient from a larger cardiac ischemic event and subsequent damage (e.g., myocardial infarction, or MI), should it occur later. Such brief periods of ischemia may be induced in a patient's heart before occlusion or during reperfusion (referred to as ischemic pre-conditioning and post-conditioning, respectively), when a cardiac ischemic event is anticipated, such as during an angioplasty procedure. Brief periods of ischemia may also be induced to a site in the patient other than the heart, such as in a limb, for similar effects (referred to as remote conditioning). Exercise is also known for inducing the cardioprotective signaling. However, such methods may not be feasible or acceptable considering the invasiveness and/or burden of the procedure given the health state of the patient.

Cardiac pacing can also provide a patient with cardioprotection. For example, brief periods of right ventricular pacing (known as intermittent pacing therapy, or IPT) change myocardial activation patterns and creates abnormal myocardial stress that has been shown to elicit cardioprotective cellular signaling. IPT has been studied for cardioprotection against ischemia resulting from occlusion of a coronary artery. It was found that, for example, IPT before occlusion or during reperfusion dramatically reduced MI size in animals, and IPT slowed or stopped increases in left ventricular size and/or mass in animal models of heart failure (i.e., showing preventative effects), but IPT did not decrease left ventricular size and/or mass in animal models with established heart failure (i.e., not showing restorative effects). Application of IPT for its preventive effects is hindered by difficulty in predicting whether and when a cardiac ischemia event may occur (except for induced cardiac ischemia such as during an angioplasty procedure).

The mechanisms of myocardial cell death resulting from chemotherapy are similar to those of MI. Examples of such mechanisms include necrosis and apoptosis resulting from generation of reactive oxygen species and creation of unfavorable cell signaling (in the mitochondria). Prevention of cardiac damage (cell death) caused by chemotherapy cardiotoxicity is highly desirable. Unlike cardiac ischemia, the timeframe of onset is known in the setting of chemotherapy as it is correlated to the therapy schedule.

Therefore, the present subject matter provides cancer patients receiving chemotherapy with cardioprotective pacing such as IPT. A pacemaker for providing a patient receiving chemotherapy with cardioprotective pacing can be a pacemaker with endocardial lead(s) or a leadless pacemaker. The pacemaker can be implanted into an at-risk patient prior to the start of the chemotherapy. The pacemaker can be configured to deliver a pacing therapy such as an IPT for a sequence of cardioprotective pacing sessions before, during, and/or after the chemotherapy. For each cardioprotective pacing session, the pacemaker may be configured to deliver a pacing sequence including alternating non-pacing and pacing periods. The non-pacing periods each include a non-pacing duration during which no pacing pulse is timed to be delivered. The pacing periods each include a pacing duration during which a plurality of pacing pulses is timed to be delivered using pacing parameters specified for effecting cardioprotection against potential myocardial injury resulting from chemotherapy.

In this document, a "chemotherapy" can include one or more treatments. Each "treatment" can include an infusion (e.g., intravenously), an injection (e.g., to the cancer, the site from which the cancer was removed, or any skeletomuscular site), an oral dosage, or any other viable manner of dosage of one or more chemotherapy drugs. For example, a chemotherapy may include a series of infusions each lasts about 1-4 hours long. The infusions may be applied to the patient about every 1-4 weeks until all the infusions have been applied. A "sequence of cardioprotective pacing sessions" can be applied for each chemotherapy. Thus, a cardiac pacing therapy, which includes a sequence of cardioprotective pacing sessions, can be applied to the patient who receives a chemotherapy, which includes a series of infusions (or other treatments), in a temporally coordinated manner. Details of such temporal coordination are discussed in this document, for example with references to FIGS. 3-8.

In various embodiments, the pacemaker for providing a patient receiving chemotherapy with cardioprotective pacing (e.g., the IPT) can be a single-purpose pacemaker made for delivering only the cardioprotective pacing or a multifunctional programmable pacemaker programmable for delivering the cardioprotective pacing. If the patient has no reason for receiving any pacing therapy other than the cardioprotective pacing (e.g., the IPT), the single-purpose pacemaker can provide a desirable small size and can be the most cost-effective. Such a single-purpose pacemaker does not need to switch between pacing modes, requires a battery having a capacity just sufficient for delivering the cardioprotective pacing, and may need only one or more external commands to control timing of the sequence of cardioprotective pacing sessions.

FIG. 1 is an illustration of an embodiment of a cardiac pacing system 100 and portions of an environment in which system 100 is used. System 100 includes an implantable system 105, an external system 115, and a wireless link 112 providing for communication between implantable system 105 and external system 115. System 100 can provide a patient receiving chemotherapy with cardioprotective pacing.

Implantable system 105 can include an implantable medical device 110 and a lead system 108. In various embodiments, implantable medical device 110 can include one or more of a pacemaker, a cardioverter/defibrillator, a cardiac resynchronization therapy (CRT) device, a cardiac remodeling control therapy (RCT) device, a neruostimulator, a drug delivery device or a drug delivery controller, and a biological therapy device, and be programmed to perform the cardioprotective pacing. In various other embodiments, implantable medical device 110 can be a dedicated cardioprotective pacing device that does not provide for any other pacing or non-pacing therapies. As illustrated in FIG. 1, implantable medical device 110 is implanted in a body 102. In various embodiments, lead system 108 includes leads for sensing physiological signals and delivering pacing pulses, cardioversion/defibrillation shocks, neurostimulation, pharmaceutical agents, biological agents, and/or other types of energy or substance for treating cardiac disorders. In various embodiments, electrodes placed in a heart 101 or other portions of body 102 can be used to sense physiological signals and deliver pacing pulses, cardioversion/defibrillation shocks, neurostimulation, pharmaceutical agents, biological agents, and/or other types of energy or substance for treating cardiac disorders. In one embodiment, lead system 108 includes one or more pacing-sensing leads each including at least one electrode placed in or on heart 101 for sensing one or more electrograms and/or delivering pacing pulses. In one embodiment, lead system 108 allows pacing pulses to be delivered to multiple atrial and/or ventricular sites.

To perform the cardioprotective pacing (e.g., IPT), implantable medical device 110 can include sensing and pacing circuitry for delivering intermittent cardiac pacing to heart 101 according to a sequence of cardioprotective pacing sessions. In some embodiments in which implantable medical device 110 is programmable for various types of therapies, in addition to the cardioprotective pacing, implantable medical device 110 also delivers one or more other cardiac pacing therapies, such a bradycardia pacing therapy, CRT, and RCT. If another pacing therapy is being delivered when a cardioprotective pacing session of the sequence of cardioprotective pacing sessions is to be started, that pacing therapy can be temporarily suspended to allow the delivery of the cardioprotective pacing and resumed upon completion of the cardioprotective pacing session. In one embodiment, implantable medical device 110 controls the delivery of one or more of other therapies such as neurostimulation therapy, drug therapy, and biologic therapy in coordination with the cardioprotective pacing.

Implantable medical device 110 can include a hermetically sealed can to house electronic circuitry that performs sensing and therapeutic functions. Examples of such electronic circuitry is discussed below with reference to FIGS. 7 and 8. In one embodiment, the electronic circuitry is entirely housed within the hermetically sealed can. In another embodiment, the electronic circuitry includes internal components housed within hermetically sealed can and external components located external to the hermetically sealed can but communicatively coupled to the internal components.

External system 115 allows a user such as a physician or other caregiver or a patient to control the operation of implantable medical device 110 and/or obtain information acquired by implantable medical device 110. External system can include a programmer, a magnet, a remoter controller, and/or any device that is capable of controlling the operation of implantable medical device 110 to any extent and/or receive any information from implantable medical device 110.

Wireless link 112 allows for communication between implantable medical device 110 and external system 115. Examples of wireless link 112 include a magnetic couple (e.g., when external system 115 includes the magnet), a Bluetooth or other short-range communication link (e.g., when external system 115 includes the remote controller), and/or an inductive or far-field radio frequency telemetry link (e.g., when external system 115 includes the programmer). When external system 115 includes the programmer, the telemetry link can be used for, for example, transmitting real-time physiological data acquired by implantable medical device 110, extracting physiological data acquired by and stored in implantable medical device 110, extracting therapy history data stored in implantable medical device 110, extracting data indicating an operational status of implantable medical device 110 (e.g., battery status and lead impedance), programming implantable medical device 110 to acquire physiological data, programming implantable medical device 110 to perform at least one self-diagnostic test (such as for a device operational status), and programming implantable medical device 110 to deliver one or more therapies.

Figure 2:
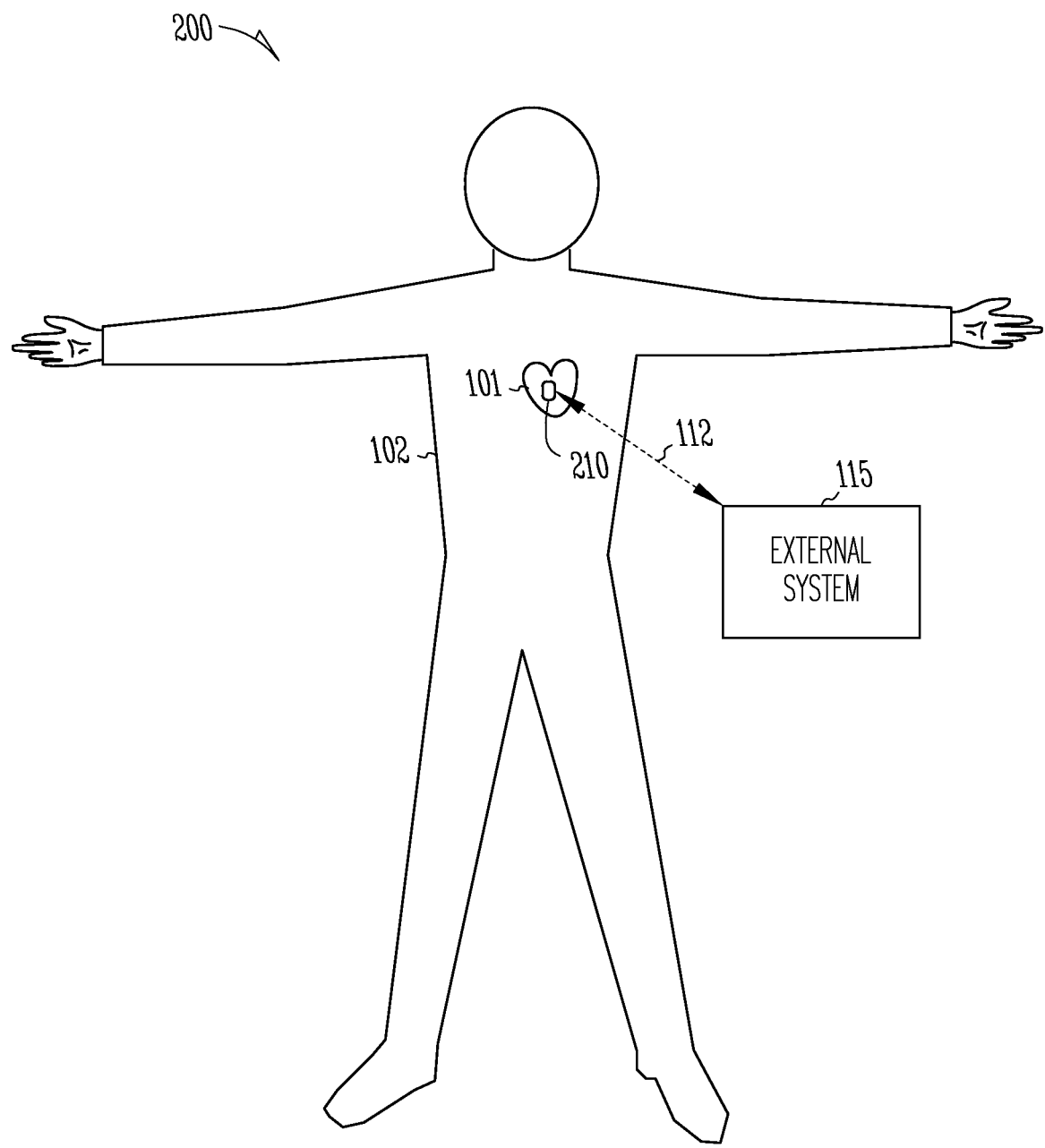
FIG. 2 is an illustration of another embodiment of the cardioprotective pacing system and portions of an environment in which the system is used.

FIG. 2 is an illustration of an embodiment of a cardioprotective pacing system 200 and portions of an environment in which system 200 is used. System 200 differs from system 100 in that its implantable system includes an implantable leadless medical device 210 that functions without a lead system. In various embodiments, system 200 can be used to perform any function of system 100 that does not need the lead system. For example, when implantable leadless medical device 210 is placed in a chamber of heart 101 (e.g., in the right ventricle), the therapy delivery site may be limited to that chamber. In various embodiments, implantable leadless medical device 210 can be placed in a chamber of heart 101 (e.g., in the right ventricle) using a percutaneous transluminal procedure. Examples for implantable leadless medical device 210 can include those discussed in U.S. Pat. No. 8,644,934 B2, "CARDIAC STIMULATION USING LEADLESS ELECTRODE ASSEMBLIES", assigned to Boston Scientific Scimed Inc., and U.S. Patent Application Publication No. US 2015/0057558 A1, "LEADLESS PACEMAKER WITH TRIPOLAR ELECTRODE", assigned to Cardiac Pacemakers, Inc., which are incorporated herein by reference in their entireties.

In various embodiments, implantable medical device 110 or implantable leadless medical device 210 can deliver cardioprotective pacing according to a cardioprotective pacing mode to a patient diagnosed of cancer and receiving chemotherapy treating the cancer. The cardioprotective pacing mode can specify alternating non-pacing and pacing periods, the non-pacing periods each including a non-pacing duration during which none of the cardiac pacing pulses is timed to be delivered, the pacing periods each including a pacing duration during which a plurality of pacing pulses of the cardiac pacing pulses is timed to be delivered. This cardioprotective pacing mode can also be referred to as an intermittent pacing mode or IPT mode.

In various embodiments, implantable medical device 110 or implantable leadless medical device 210 can be a single-mode cardioprotective pacemaker that is pre-configured for operation only under the cardioprotective pacing mode for controlling delivery of the cardiac pacing pulses to effect cardioprotection against potential myocardial injury resulting from chemotherapy. The single-mode cardioprotective pacemaker may not be reconfigurable (e.g., not re-programmable or otherwise modifiable) for delivering the cardiac pacing pulses according to a pacing mode other than the cardioprotective pacing mode. The single-mode cardioprotective pacemaker can have programmability limited to adjusting parameters used for controlling delivery of the cardiac pacing pulses under the cardioprotective pacing mode.

In various other embodiments, implantable medical device 110 or implantable leadless medical device 210 can be a multi-mode programmable pacemaker that can be programmed for delivering cardiac pacing pulses to the patient according to the cardioprotective pacing mode. The multi-mode programmable pacemaker is reconfigurable (e.g., re-programmable or otherwise modifiable) for delivering the cardiac pacing pulses according to various cardiac pacing modes including the cardioprotective pacing mode. Examples of the various pacing modes in addition to the cardioprotective pacing mode can include various anti-bradycardia, anti-tachycardia, CRT, and RCT pacing modes. The multi-mode programmable pacemaker can have programmability allowing for adjusting parameters used for controlling delivery of cardiac pacing pulses under each pacing mode selected from the various cardiac pacing modes.

In various other embodiments, implantable medical device 110 or implantable leadless medical device 210 can be manually commanded (by manually issuing a sequence stating command) to start the sequence of cardioprotective pacing sessions without using a conventional pacemaker programmer. For example, the patient or his physician or other caregiver can manually trigger the start of the sequence of cardioprotective pacing sessions before, during, or after the chemotherapy infusion. Such manual triggering can be done, for example, with the magnet or the remote controller, while the programmer, when available, can also be used. Each of implantable medical device 110 or implantable leadless medical device 210 can include one or more safety features limiting the response to the manual triggering according to one or more safety rules. For example, the sequence of cardioprotective pacing sessions can be triggered only once for a specified time interval. In some embodiments, if the pacing sessions are automatically triggered by the pacemaker according to a specified pacing sessions schedule once the cardioprotective pacing period is triggered, the pacemaker can be manually commanded to interrupt or stop the sequence of cardioprotective pacing sessions.

Figure 3:
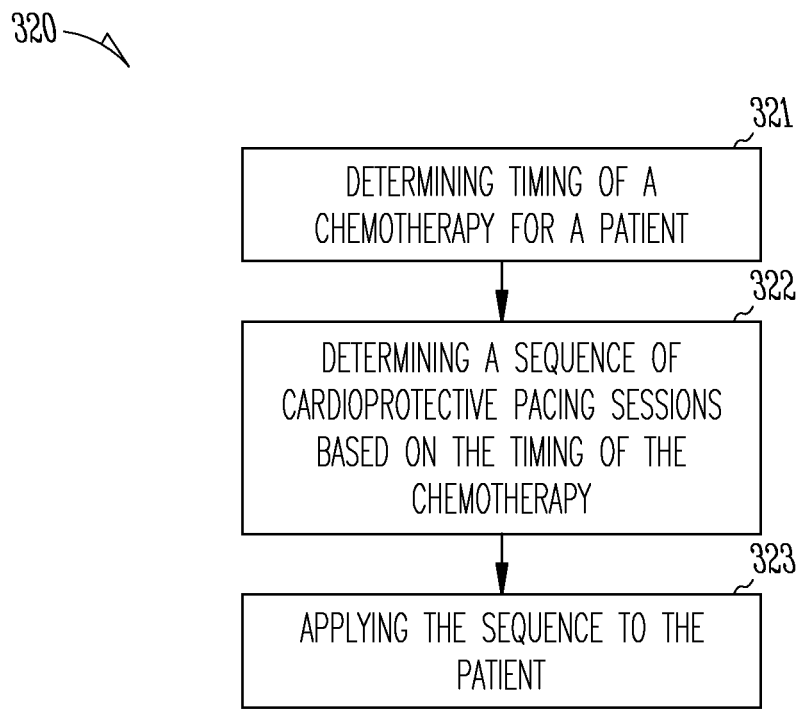
FIG. 3 is a flow chart illustrating an embodiment of a method for cardioprotective pacing for a patient receiving chemotherapy.

FIG. 3 is a flow chart illustrating an embodiment of a method 320 for cardioprotective pacing for a patient receiving chemotherapy. Method 320 can be performed using a pacemaker, such as implantable medical device 110 or implantable leadless medical device 210. Implantable medical device 110 or implantable leadless medical device 210 can be the single-mode cardioprotective pacemaker pre-configured for performing method 320 or the multi-mode programmable pacemaker programmed for performing method 320.

At 321, timing of the chemotherapy is determined. The determination can include receiving the treatment schedule for the chemotherapy from the physician attending the cancer patient. The chemotherapy can include one or more treatments (e.g., one or more infusions). The timing of the chemotherapy can include a schedule for the one or more treatments, which can specified one or more of a time when the chemotherapy (or the first treatment of the chemotherapy) is to be started, a time when the chemotherapy (or the last treatment of the chemotherapy) is to end, a starting time for each of the one or more treatments, the ending time for each of the one or more treatments, the duration for each of the one or more treatments, or a frequency of the treatments. At 322, a sequence of cardioprotective pacing sessions based on the timing of the chemotherapy is determined. This includes determination of when the sequence of cardioprotective pacing sessions is to be started and ended relative to the timing of the chemotherapy as well as various adjustable pacing parameters. In various embodiments in which the chemotherapy includes a series of treatments, the cardioprotective pacing sessions can be synchronized to the treatments. For example, a cardioprotective pacing session can be started before, during, and/or after each treatment of the chemotherapy. In various other embodiments in which the chemotherapy includes a series of treatments, the cardioprotective pacing sessions are not synchronized to the treatments, but for example are started on a periodical basis that can be independently timed. At 323, the sequence of cardioprotective pacing sessions is applied to the patient. Each session of the sequence of cardioprotective pacing sessions includes alternating non-pacing and pacing periods. The non-pacing periods each include a non-pacing duration during which no pacing pulse is timed to be delivered. The pacing periods each include a pacing duration during which a plurality of pacing pulses is timed to be delivered using pacing parameters set for effecting cardioprotection of patient against potential myocardial injury resulting from the chemotherapy.

Figure 4:
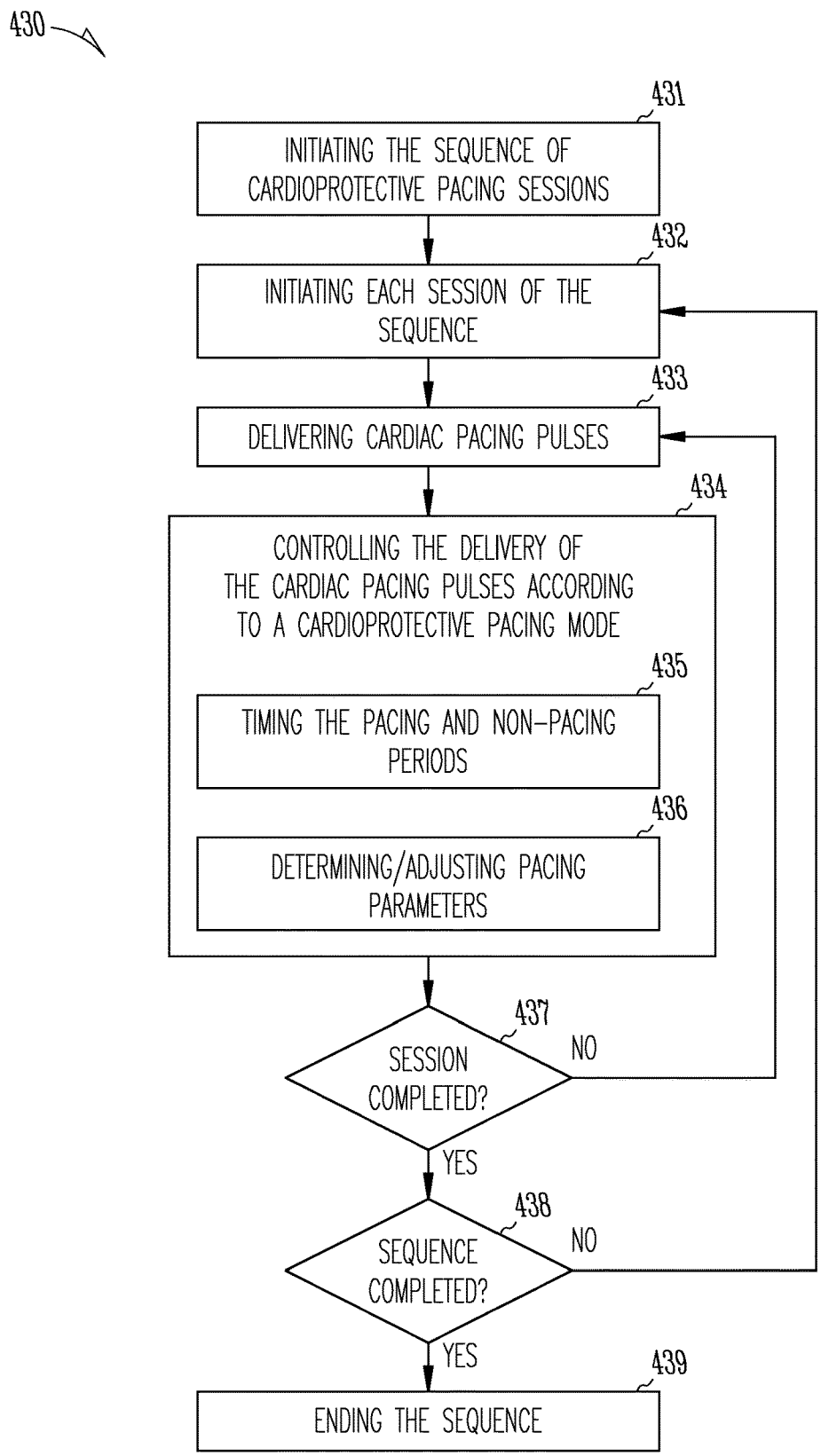
FIG. 4 is a flow chart illustrating an embodiment of the method for applying the cardioprotective pacing to the patient receiving chemotherapy.

FIG. 4 is a flow chart illustrating another embodiment of a method 430 for applying the cardioprotective pacing to the patient receiving chemotherapy. Method 430 can be performed as step 323 of method 320. Method 430 can be performed using a pacemaker, such as implantable medical device 110 or implantable leadless medical device 210. Implantable medical device 110 or implantable leadless medical device 210 can be the single-mode cardioprotective pacemaker pre-configured for performing method 430 or the multi-mode programmable pacemaker programmed for performing method 430.

At 430, the sequence of cardioprotective pacing sessions is initiated. The sequence of cardioprotective pacing sessions can be initiated in response to a sequence starting command. The sequence starting command can be an external sequence starting command in any formed that can be received by the pacemaker. For example, the external sequence starting command can be a magnetic signal produced by a magnet brought to proximity of the pacemaker. The external sequence starting command can also be a remote control signal produced by a remote controller such as a dedicated remote controller for the pacemaker or a generic device configured to communicate with the pacemaker, such as a computer or a cellphone. A pacemaker programmer can also be used to produce and transmit the remote control signal. In some embodiments, the remote controller or the pacemaker programmer can also be used to present status of operation of the pacemaker including timing for the sequence of cardioprotective pacing sessions, whether one of the cardioprotective pacing sessions is ongoing, and or the number of the cardioprotective pacing sessions delivered and/or remaining. The sequence of cardioprotective pacing sessions is initiated based on the timing of the chemotherapy.

Figure 5:
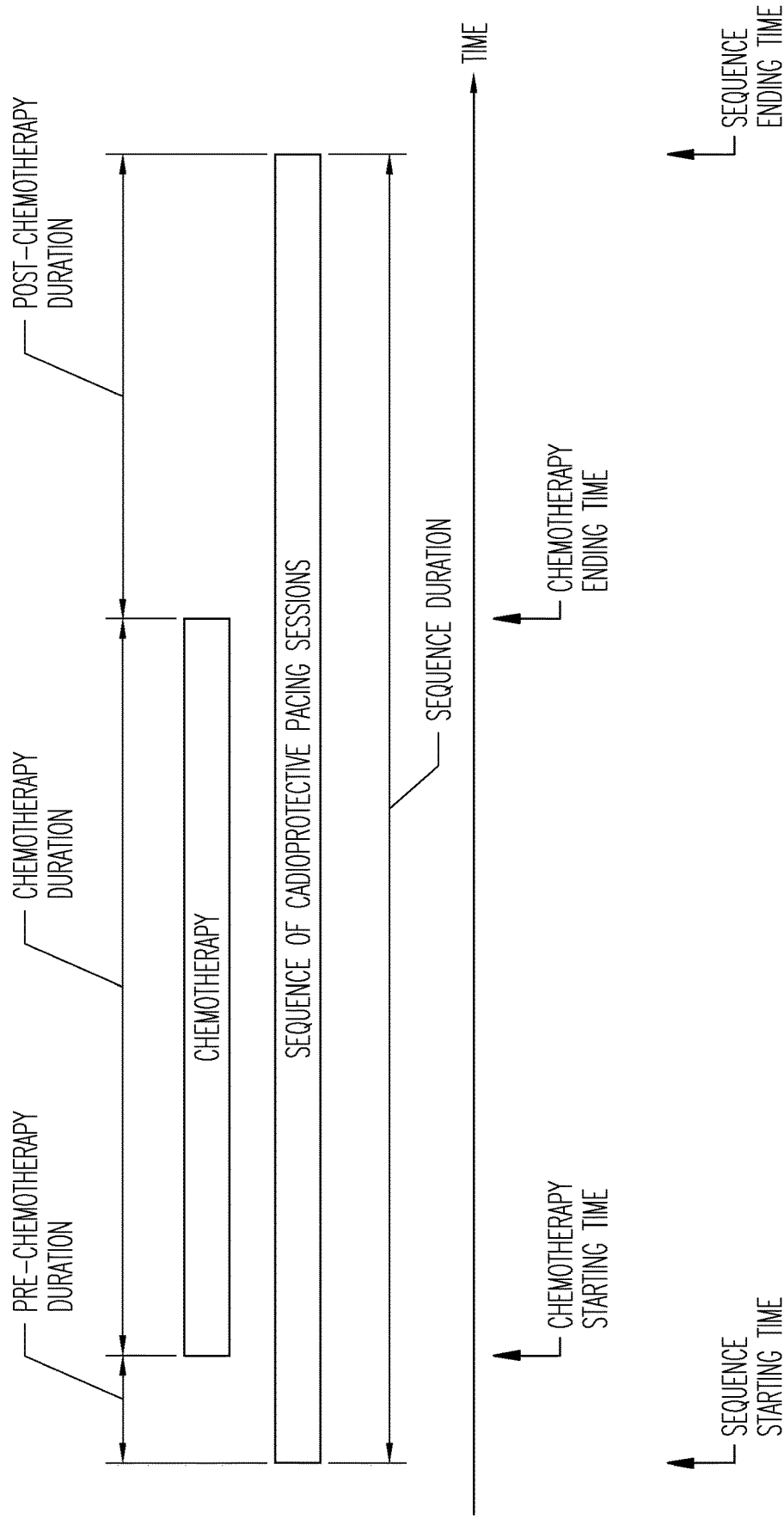
FIG. 5 is a timing diagram illustrating an embodiment of a sequence of cardioprotective pacing sessions timed based on timing of a chemotherapy.

FIG. 5 is a timing diagram illustrating an embodiment of the sequence of cardioprotective pacing sessions timed based on the timing of a chemotherapy. The sequence of cardioprotective pacing sessions is initiated at a beginning of a pre-chemotherapy duration ending with the chemotherapy starting time. The pre-chemotherapy duration can be about 1 day (e.g., 1 to 30 days, with 1 day being a specific example). The sequence of cardioprotective pacing sessions is ended at an end of a post-chemotherapy duration starting with the chemotherapy ending time. The post-chemotherapy duration can be about 6 weeks (e.g., 1 to 24 weeks, with 6 weeks being a specific example). The timing as illustrated in FIG. 5 represents an example, rather than a limitation, of timing of the sequence of cardioprotective pacing sessions determined relative to the timing of the chemotherapy. In various embodiments, as determined by the physician or another qualified professional, the sequence of cardioprotective pacing sessions can be initiated before the chemotherapy starting time (pre-chemotherapy duration>0), at the chemotherapy starting time (pre-chemotherapy duration=0), between the chemotherapy starting time and the chemotherapy ending time (−chemotherapy duration<pre-chemotherapy duration<0), at the chemotherapy ending time (pre-chemotherapy duration=−chemotherapy duration), or after the chemotherapy ending time (pre-chemotherapy duration<−chemotherapy duration), and can be ended before the chemotherapy starting time (post-chemotherapy duration<−chemotherapy duration), at the chemotherapy starting time (post-chemotherapy duration=−chemotherapy duration), between the chemotherapy starting time and the chemotherapy ending time (−chemotherapy duration<post-chemotherapy duration<0), at the chemotherapy ending time (post-chemotherapy duration=0), or after the chemotherapy ending time (post-chemotherapy duration>0). The total length of the sequence of cardioprotective pacing sessions, the sequence duration, is the sum of the pre-chemotherapy duration, the chemotherapy duration, and the post-chemotherapy duration. The chemotherapy duration can be the total time interval between the beginning of the first treatment and the end of the last treatment of the series of treatments (e.g., infusions) of a chemotherapy.

Figure 6:
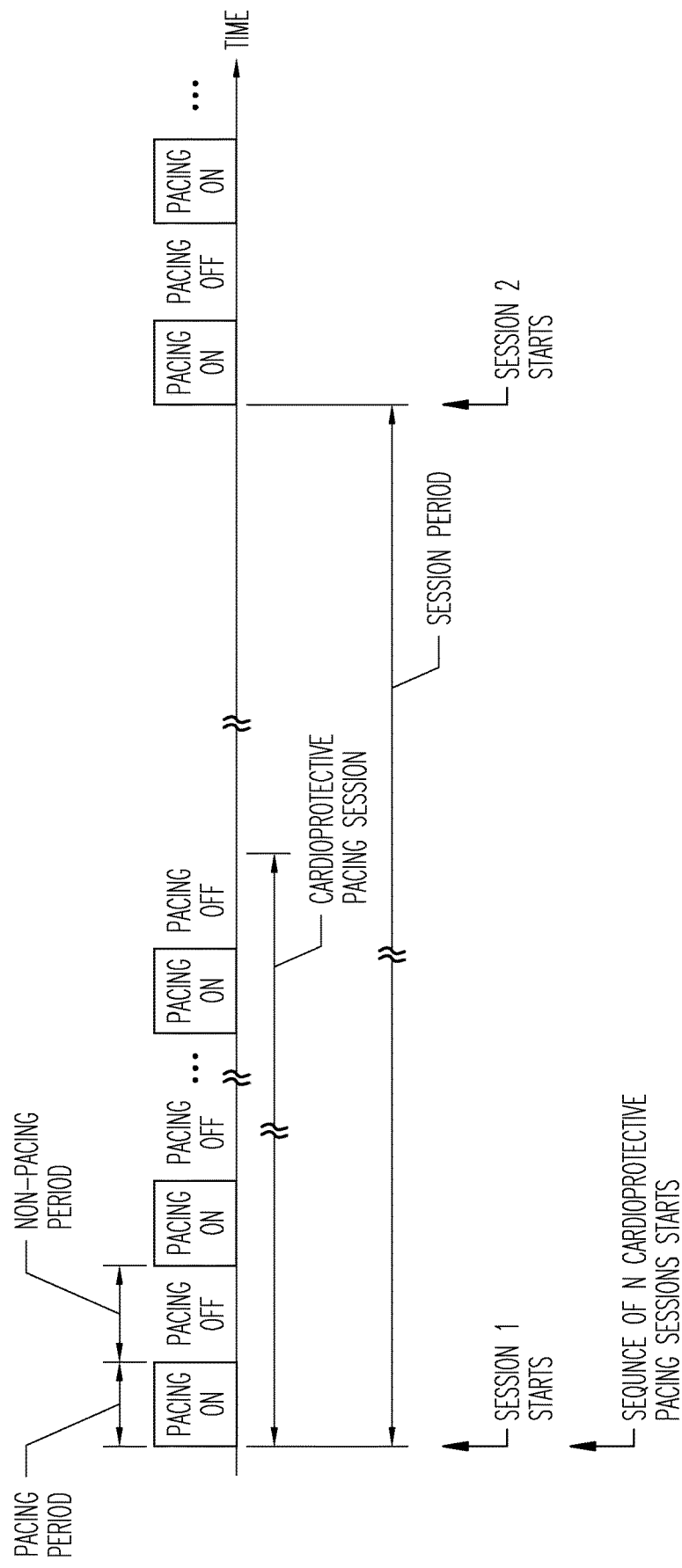
FIG. 6 is a timing diagram illustrating an embodiment of a sequence of cardioprotective pacing sessions for protecting the heart from potential injuries resulting from a chemotherapy.

Referring back to FIG. 4. At 432, each session of the sequence of cardioprotective pacing sessions is initiated. The sessions can be initiated according to a pacing sessions schedule. FIG. 6 is a timing diagram illustrating an embodiment of the sequence of cardioprotective pacing sessions. In various embodiments, a session of the sequence of cardioprotective pacing sessions can be initiated manually in response to an external session starting command received by the pacemaker. The external session starting command can be issued in the same manner as the external sequence starting command. In some embodiments, each pacing session can be manually triggered once during a specified time interval (e.g., 8 am to 5 µm with 11 am being a specific example). For example, the pacing session can be manually triggered by the physician, other caregiver, or the patient prior to start of each treatment of the chemotherapy. In various embodiments, a session of the sequence of cardioprotective pacing sessions can be initiated automatically by the pacemaker according to the pacing sessions schedule stored in the pacemaker. When the pacing sessions are not synchronized to the treatments of chemotherapy, the pacing sessions schedule can specify a session frequency of about 1 session per day (e.g., 1 to 4 sessions/day with 1 sessions/day being a specific example). The session frequency corresponds to the session period in FIG. 6 (session frequency=1/session period). The pacing sessions schedule can also specify a time of a day for initiating each session of the sequence of pacing sessions (e.g., a time at night when the patient is likely sleeping). When the pacing sessions are synchronized to the treatments of chemotherapy, the pacing sessions schedule can be based on a schedule of the series of treatments of the chemotherapy.

FIG. 7 is a timing diagram illustrating an embodiment of cardioprotective pacing sessions each timed based on a treatment of a chemotherapy. In the illustrated embodiment, the cardioprotective pacing sessions are synchronized to the treatments of the chemotherapy, and each cardioprotective pacing session starts prior to a treatment of chemotherapy. In various embodiments, one or more cardioprotective pacing session can be started before, during, and/or after a treatment of chemotherapy. In various embodiment, one or more cardioprotective pacing sessions can be scheduled for each treatment of the chemotherapy, each of these sessions can start before the treatment (e.g., 0 to 6 hours before the treatment starts, with 15 minutes being a specific example), during the treatment (e.g., 0 to 2 hours after the treatment starts, with 1 hour being a specific example), or after the treatment (e.g., 0 to 6 hours after the treatment ends, with 15 minutes being a specific example). FIG. 8 is a timing diagram illustrating an embodiment of cardioprotective pacing sessions timed to be applied periodically. In the illustrated embodiment, the cardioprotective pacing sessions are not synchronized to the treatments of the chemotherapy, and are applied periodically (e.g., 1 to 4 sessions/day with 1 sessions/day being a specific example).

Referring back to FIG. 4. At 433, cardiac pacing pulses are delivered to the patient during each of the cardioprotective pacing sessions according to the cardioprotective pacing mode for controlling delivery of the cardiac pacing pulses to effect cardioprotection against potential myocardial injury resulting from chemotherapy. In various embodiments, the cardiac pacing pulses can be delivered from an implantable pacemaker (such as implantable medical device 110) through one or more leads each including one or more electrodes (such as lead system 108). In various embodiments, the cardiac pacing pulses can be delivered from a leadless pacemaker (such as implantable leadless medical device 210) through electrodes incorporated onto the leadless pacemaker.

At 434, the delivery of the cardiac pacing pulses is controlled according to the cardioprotective pacing mode. The controlling includes timing the pacing and non-pacing periods during each cardioprotective pacing session at 435 (in response to the initiation of the session) and determining and/or adjusting pacing parameters at 436. As illustrated in FIG. 6, the cardioprotective pacing mode specifies a number of alternating non-pacing and pacing periods. The non-pacing periods ("PACING OFF") each include a non-pacing duration during which none of the cardiac pacing pulses is timed to be delivered. The pacing periods ("PACING ON") each include a pacing duration during which a plurality of pacing pulses of the cardiac pacing pulses is timed to be delivered. Each session of the sequence of cardioprotective pacing sessions can include 3 to 15 pairs of alternating non-pacing and pacing periods, with 3 pairs being a specific example. The non-pacing duration can be 30 seconds to 30 minutes, with 3 minutes being a specific example). The pacing duration can be 30 seconds to 30 minutes, with 3 minutes being a specific example.

The pacing parameters are determined to effect cardioprotection against potential myocardial injury resulting from chemotherapy. One or more parameters of the pacing parameters can be determined or adjusted automatically by the pacemaker. In various embodiments, one or more cardiac signals are sensed, the one or more parameters of the pacing parameters are determined or adjusted based on the sensed one or more cardiac signals. In one various embodiments, the cardiac pacing pulses can be delivered to the right ventricle with an adjustable pacing rate and/or atrioventricular delay providing for relative atrial synchrony (if desirable). For example, the pacing rate can be adjusted to be about 15% faster than the patient's intrinsic ventricular rate (e.g., 10 to 100% faster, with 15% being a specific example), and/or the atrioventricular delay can be adjusted to about 50% of the patient's intrinsic atrioventricular interval (e.g., 10 to 100% of the patient's intrinsic atrioventricular interval, with 50% being a specific example). In one embodiment, the cardiac pacing pulses are delivered to the right ventricle without using an atrioventricular synchrony.

If the session is not completed at 437 (based on the number of the pairs of alternating pacing and non-pacing periods specified for the session), the cardiac pacing pulses continue to be delivered at 432 according to the pacing sessions schedule. In some embodiments, each session of the sequence of cardioprotective sessions and/or the sequence itself can be suspended or terminated in response to certain event. For example, one or more signals indicative of an inhibiting event can be sensed. The inhibiting event includes any event indicating that continuing delivery of the pacing pulses under the cardioprotective pacing mode may be ineffective and/or detrimental to the patient's health. In response to a detection of the inhibiting event, the delivery of the cardiac pacing pulses during the sequencer of cardioprotective pacing session can be cancelled or rescheduled (e.g., delayed until the inhibiting event is no longer detected), and/or an ongoing cardioprotective pacing session can be stopped. In various embodiments, the pacemaker can include one or more sensors and use one or more sensed signals to inhibit pacing when one or more inhibiting events are detected from the one or more sensed signals. For example, the pacemaker can (1) include a heart rate sensor to sense the patient's heart rate and inhibit the cardioprotective pacing when the sensed heart rate exceeds an upper threshold or falls below a lower threshold, (2) include a posture sensor to sense the patient's posture and inhibit the cardioprotective pacing when the sensed posture indicates that the patient is at an upright posture, and/or (3) include an activity sensor to sense the patient's physical activity level and inhibit the cardioprotective pacing when the sensed activity level exceeds a threshold. An inhibited sequence of cardioprotective pacing sessions, or any inhibited portion of the sequence, may be delivered after the one or more sensed signals indicate that an undesirable period has ended. Other types of sensors can be used for sensing and detecting any types of inhibiting event.

If the sequence of cardioprotective pacing sessions is not completed at 438 (based on the number of the cardioprotective pacing sessions specified in the pacing sessions schedule), the next session is initiated at 432 according to the pacing sessions schedule. If the sequence of cardioprotective pacing sessions is completed at 438, the sequence is ended at 439. In various embodiments, the sequence of cardioprotective pacing sessions can be ended automatically by the pacemaker based on the chemotherapy duration or the chemotherapy ending time. In various embodiments, the sequence of cardioprotective pacing sessions can also be ended in response to an external sequence ending command received by the pacemaker. The external sequence ending command can be issued in the same manner as the external sequence starting command. The external sequence end command can be used to stop the sequence of cardioprotective pacing sessions for an unexpected reason, such as early termination of the chemotherapy or a medical condition for which continuing the cardioprotective pacing may be detrimental to the health of the patient.

Figure 9:
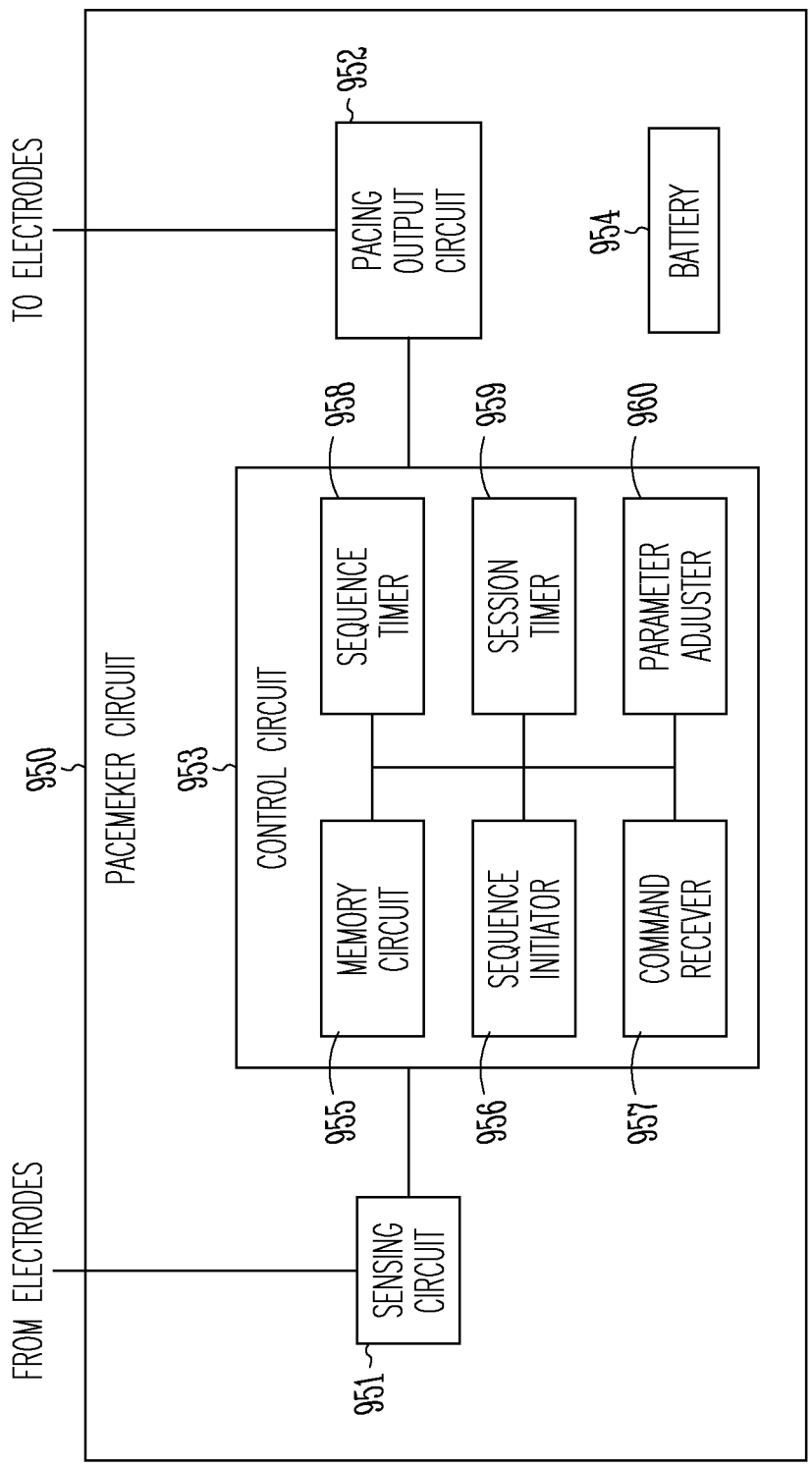
FIG. 9 is a block diagram illustrating an embodiment of a circuit of a cardioprotective pacemaker.

FIG. 9 is a block diagram illustrating an embodiment of a pacemaker circuit 950, which represents an example of portions of the electronic circuitry of implantable medical device 110 or implantable leadless medical device 210. In one embodiment, pacemaker circuit 950 is configured for delivering cardiac pacing pulses to a patient diagnosed of cancer and receiving chemotherapy treating the cancer, such as being used to perform method 430. In the illustrated embodiment, pacemaker circuit 950 includes a sensing circuit 951 to sense one or more cardiac signals, a pacing output circuit 952 to produce and deliver cardiac pacing pulses, a control circuit 953 to control the delivery of the cardiac pacing pulses using pacing parameters according to the cardioprotective pacing mode (as discussed above), and a battery 954 to supply power needed for the operations of pacemaker circuit 950.

Control circuit 953 cab include a memory circuit 955, a sequence initiator 956, a command receiver 957, a sequence timer 958, a session timer 959, and a parameter adjuster 960. Memory circuit 955 store information required to operate pacemaker circuit 950 under the cardioprotective pacing mode, including the pacing parameters and the pacing sessions schedule. Sequence initiator 956 can initiate the sequence of cardioprotective pacing sessions in response to the sequence starting command. Command receiver 957 can receive the sequence starting command, which can be a magnetic or electromagnetic signal produced by an external device such as the magnet, the remote controller, or the programmer of external system 115. Sequence timer 958 can initiate each session of the sequence of cardioprotective pacing sessions after the initiation of the sequence. In various embodiments, sequence timer 958 can initiate each session according to the stored pacing sessions schedule. In some embodiments, sequence timer 958 can initiate each session in response to a session starting command, and command receiver 957 can also receive the session starting command. Sequence timer 958 can also end the sequence of cardioprotective pacing sessions (e.g., to stop initiating new sessions of the sequence of cardioprotective pacing sessions). In various embodiments, sequence timer 958 can end the sequence according to the stored pacing sessions schedule (e.g., by timing the sequence duration or counting the number of cardioprotective pacing sessions). In some embodiments, sequence timer 958 can end the sequence in response to a sequence ending command, and command receiver 957 can also receive the session ending command. Session timer 959 can time the pacing and non-pacing periods during each session of the sequence of cardioprotective pacing sessions. Parameter adjuster 960 can adjust the pacing parameters for effecting cardioprotection against potential myocardial injury resulting from chemotherapy. In various embodiments, parameter adjuster 960 adjusts the one or more parameters based on the sensed one or more cardiac signals. Battery 954 can supply power for the operation of pacemaker circuit 950. In embodiments in which pacemaker circuit 950 is part of the single-mode cardioprotective pacemaker that is pre-configured for operation only under the cardioprotective pacing mode, battery 954 can be configured to have an energy capacity sufficient for delivering the cardioprotective pacing to a patient receiving chemotherapy and not substantially beyond. For example, the energy capacity of battery 954 can be determined based on an estimation the energy required for delivering the cardioprotective pacing and a safety margin such as 10 to 100 percent, with 50 percent as a specific example. The determination of battery capacity can also include considerations of factors contributing to extension and/or reapplication of chemotherapy due to non-responsiveness of the patient to a particular drug and/or relapse of the cancer, such as based on statistical data.

Figure 10:
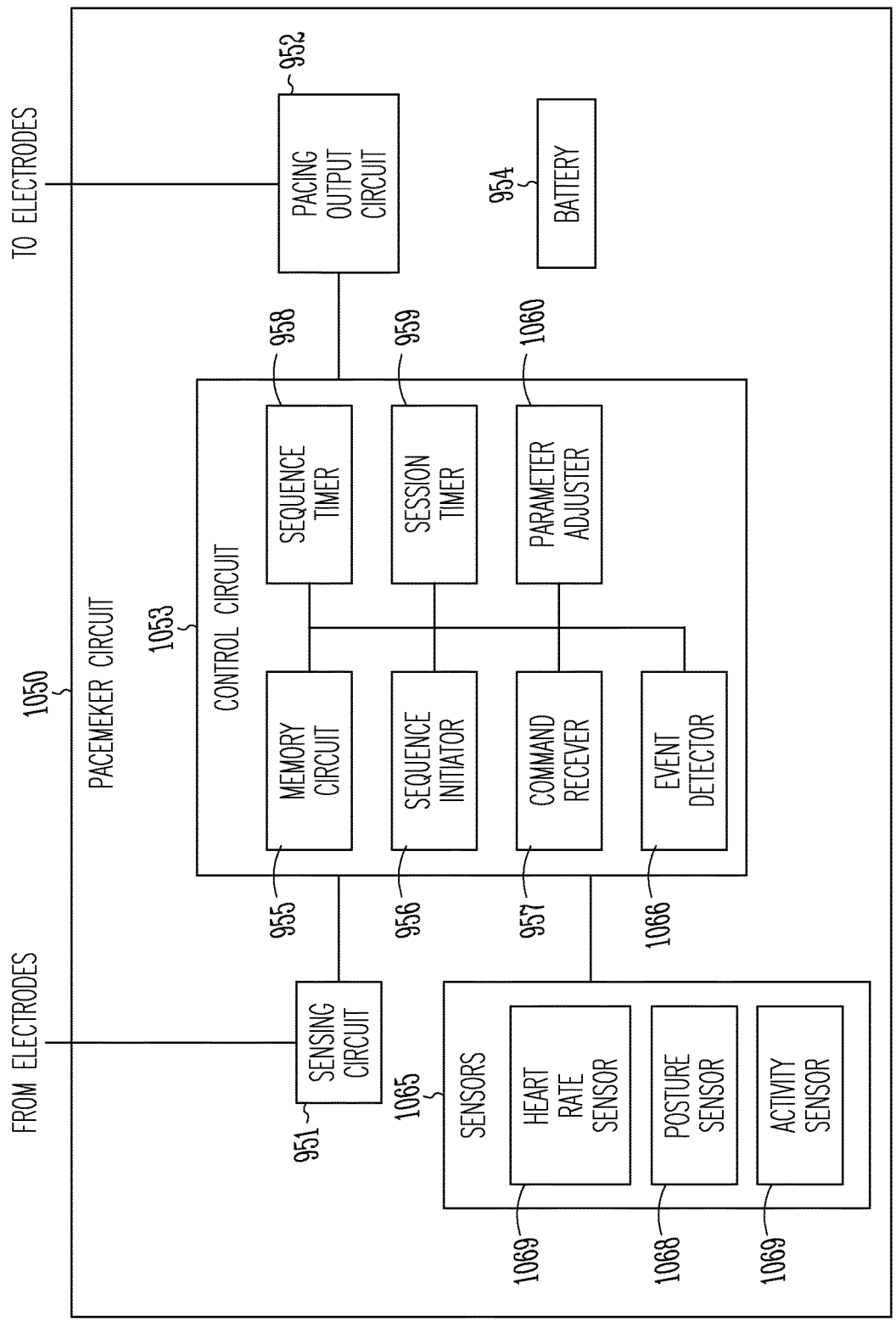
FIG. 10 is a block diagram illustrating an embodiment of another circuit of a cardioprotective pacemaker.

FIG. 10 is a block diagram illustrating an embodiment of a pacemaker circuit 1050, which represents another example of portions of the electronic circuitry of implantable medical device 110 or implantable leadless medical device 210. In one embodiment, pacemaker circuit 1050 is configured for delivering cardiac pacing pulses to a patient diagnosed of cancer and receiving chemotherapy treating the cancer, such as being used to perform method 430. In the illustrated embodiment, pacemaker circuit 1050 includes sensing circuit 951 to sense one or more cardiac signals, pacing output circuit 952 to produce and deliver cardiac pacing pulses, a control circuit 1053 to control the delivery of the cardiac pacing pulses using pacing parameters according to the cardioprotective pacing mode (as discussed above), sensors 1065 to sense one or more signals (in addition to the one or more cardiac signals), and battery 954 to supply power needed for the operations of pacemaker circuit 1050. In other words, pacemaker circuit 1050 includes elements of pacing circuit 750 and sensors 1065, with control circuit 1053 controlling the delivery of the cardiac pacing pulses using the one or more signal sensed by sensors 1065 in addition to the parameters used by control circuit 953.

In the illustrated embodiment, sensors 1065 includes a heart rate sensor 1067, a posture sensor 1068, and an activity sensor 1069. In various embodiments, sensors 1065 can include any one or any combination of heart rate sensor 1067, posture sensor 1068, activity sensor 1069, and other sensors capable of sensing one or more signals that can be used to control the delivery of the cardiac pacing pulses using pacing parameters according to the cardioprotective pacing mode. In addition to memory circuit 955, sequence initiator 956, command receiver 957, sequence timer 958, session timer 959, and a parameter adjuster 1060, control circuit 1053 includes an event detector 1066 to detect an adjustment event using the one or more signals sensed by sensors 1065. The adjustment event is indicative of a need for adjusting the pacing parameters, and parameter adjuster 1060 can adjust the pacing parameters in response to a detection of the adjustment event. The adjustment event can be an inhibiting event for stopping the delivery of the cardiac pacing pulses. Parameter adjuster 1060 can inhibit or reschedule (e.g., delaying) the delivery of the cardiac pacing pulses during each cardioprotective pacing session in response to a detection of the inhibiting event. For example, parameter adjuster 1060 can allow the inhibited delivery of the cardiac pacing pulses to be delivered after the inhibiting event is no longer detected by the pacing inhibitor. In the illustrated embodiment, heart rate sensor 1067 can sense the patient's intrinsic heart rate (e.g., ventricular rate), and event detector 1066 can detect the inhibiting event when the sensed heart rate exceeds an upper threshold or falls below a lower threshold. Posture sensor 1068 can sense the patient's posture, and event detector 1066 can detect the inhibiting event when the sensed posture indicates that the patient is at an upright posture. Activity sensor 1069 can sense the patient's physical activity level, and event detector 1066 can detect the inhibiting event when the sensed activity level exceeds a threshold.

In various embodiments, pacemaker circuit 950 and 1050 may each be implemented using a combination of hardware and software. For example, control circuits 953 and 1053 may each be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for protecting a patient diagnosed of cancer from cardiac injury resulting from a chemotherapy treating the cancer, comprising:

initiating a sequence of cardioprotective pacing sessions based on timing of the chemotherapy, including timing the initiation of the sequence relative to a chemotherapy starting time; and delivering cardiac pacing pulses to the patient during each session of the cardioprotective pacing sessions according to a cardioprotective pacing mode for controlling delivery of the cardiac pacing pulses to effect cardioprotection against potential myocardial injury resulting from the chemotherapy, the cardioprotective pacing mode specifying alternating non-pacing and pacing periods, the non-pacing periods each including a non-pacing duration during which none of the cardiac pacing pulses is timed to be delivered, the pacing periods each including a pacing duration during which a plurality of pacing pulses of the cardiac pacing pulses is timed to be delivered.

2. The method of claim 1, wherein delivering the cardiac pacing pulses comprises delivering the cardiac pacing pulses from an implantable pacemaker, and initiating the sequence of cardioprotective pacing sessions comprises initiating the sequence of cardioprotective pacing sessions is response to a sequence starting command received by the implantable pacemaker.

3. The method of claim 2, wherein delivering the cardiac pacing pulses from the implantable pacemaker comprises delivering the cardiac pacing pulses from an implanted intracardiac leadless pacemaker.

4. The method of claim 1, further comprising determining the timing of the chemotherapy including the chemotherapy starting time, and wherein initiating the sequence of cardioprotective pacing sessions comprises initiating the sequence of cardioprotective pacing sessions at a beginning of a pre-chemotherapy duration ending with the chemotherapy starting time.

5. The method of claim 4, wherein determining the timing of the chemotherapy further comprises determining a chemotherapy ending time, and further comprising ending the sequence of cardioprotective pacing sessions at an end of a post-chemotherapy duration starting with the chemotherapy ending time.

6. The method of claim 1, further comprising initiating each session of the sequence of cardioprotective pacing sessions according to a session frequency.

7. The method of claim 1, wherein the chemotherapy comprises a series treatments, and further comprising:
determining the timing of the chemotherapy including a time for applying each treatment of the series of treatments; and
initiating one or more sessions of the sequence of cardioprotective pacing sessions based on the time for applying the each treatment.

8. The method of claim 7, wherein initiating the one or more sessions comprises initiating one session of the one or more sessions before the each treatment starts.

9. The method of claim 7, wherein initiating the one or more sessions comprises initiating one session of the one or more sessions after the each treatment ends.

10. The method of claim 1, further comprising:
sensing one or more cardiac signals; and
adjusting one or more pacing parameters for effecting the cardioprotection against potential myocardial injury resulting from the chemotherapy based on the sensed one or more cardiac signals, the one or more pacing parameters controlling the delivery of the cardiac pacing pulses according to the cardioprotective pacing mode.

11. The method of claim 10, further comprising detecting a heart rate from the one or more cardiac signals, and wherein adjusting the one or more pacing parameters comprises setting a pacing rate to a rate substantially higher than the detected heart rate.

12. The method of claim 10, further comprising detecting an intrinsic atrioventricular interval from the one or more cardiac signals, and wherein adjusting the one or more pacing parameters comprises setting an atrioventricular delay to a time interval substantially shorter than the detected intrinsic atrioventricular interval.

13. The method of claim 1, further comprising:
sensing one or more signals from the patient;
detecting an inhibiting event using the sensed one or more signals; and
inhibiting or rescheduling the delivery of the cardiac pacing pulses during the sequence of cardioprotective pacing session in response to a detection of the inhibiting event.

14. A system for delivering cardiac pacing pulses to a patient diagnosed of cancer and receiving chemotherapy treating the cancer, comprising:
an implantable cardioprotective pacemaker pre-configured for operation only under a cardioprotective pacing mode for controlling delivery of the cardiac pacing pulses to effect cardioprotection against potential myocardial injury resulting from chemotherapy, the cardioprotective pacing mode specifying alternating non-pacing and pacing periods, the non-pacing periods each including a non-pacing duration during which none of the cardiac pacing pulses is timed to be delivered, the pacing periods each including a pacing duration during which a plurality of pacing pulses of the cardiac pacing pulses is timed to be delivered,
wherein the pacemaker is not reconfigurable for delivering the cardiac pacing pulses according to a pacing mode other than the cardioprotective pacing mode.

15. The system of claim 14, wherein the pacemaker comprises:
a pacing output circuit configured to deliver the cardiac pacing pulses; and
a control circuit configured to control the delivery of the cardiac pacing pulses using pacing parameters according to the cardioprotective pacing mode, the control circuit including:
a sequence initiator configured to initiate a sequence of cardioprotective pacing sessions in response to a sequence starting command; and
a command receiver configured to receive the sequence starting command.

16. The system of claim 15, further comprising an external device configured to wirelessly communicate with the pacemaker and to generate the sequence starting command.

17. The system of claim 15, wherein the control circuit further comprises:
a sequence timer configured to initiate each session of the sequence of cardioprotective pacing sessions after the initiation of the sequence of cardioprotective pacing sessions; and
a session timer configured to time the pacing and non-pacing periods during the each session in response to the initiation of the each session.

18. The system of claim 17, wherein pacemaker further includes a sensing circuit configured to sense one or more cardiac signals from the patient, and the control circuit further comprises a parameter adjuster to adjust the pacing parameters based on the sensed one or more cardiac signals such that the delivery of the cardiac pacing pulses effects the cardioprotection against potential myocardial injury resulting from the chemotherapy.

19. The system of claim 18, further comprising one or more sensors configured to sense one or more patient state signals, and wherein the control circuit further comprises an event detector configured to detect an inhibit event using the one or more signals, and the parameter adjuster is configured to inhibit or reschedule the delivery of the cardiac pacing pulses during a session of the sequence of cardioprotective pacing session in response to a detection of the inhibiting event.

20. The system of claim 19, wherein the one or more sensors comprises one or more of a heart rate sensor configured to sense the patient's heart rate, a posture sensor configured to sense the patient's posture, or an activity sensor configured to sense the patient's physical activity level, and the event detector is configured to detect the inhibit event in response to one or more of the sensed heart rate exceeding an upper threshold or falls below a lower threshold, the sensed posture indicating that the patient is at an upright posture, or the sensed activity level exceeding a threshold activity level.

* * * * *